(12) United States Patent
Minami

(10) Patent No.: US 7,133,574 B2
(45) Date of Patent: Nov. 7, 2006

(54) METHOD FOR RECOGNIZING POSITION OF HONEYCOMB STRUCTURE

(75) Inventor: Takao Minami, Kuwana (JP)

(73) Assignee: Denso Corporation (JP)

( * ) Notice: Subject to any disclaimer, the term of this patent is extended or adjusted under 35 U.S.C. 154(b) by 590 days.

(21) Appl. No.: 10/225,292

(22) Filed: Aug. 22, 2002

(65) Prior Publication Data
US 2003/0048941 A1   Mar. 13, 2003

(30) Foreign Application Priority Data
Sep. 10, 2001   (JP)   ............................. 2001-273773

(51) Int. Cl.
*G06K 9/36*   (2006.01)
(52) U.S. Cl. .................. 382/291; 382/103; 382/106; 382/141; 382/199; 356/606; 348/50; 348/136
(58) Field of Classification Search ................ 382/291, 382/103, 106, 151, 141, 199; 356/602, 606; 348/50, 136
See application file for complete search history.

(56) References Cited

U.S. PATENT DOCUMENTS

| | | | | |
|---|---|---|---|---|
| 4,213,117 A | * | 7/1980 | Kembo et al. | .............. 382/145 |
| 4,513,316 A | * | 4/1985 | Kobayashi et al. | .......... 348/133 |
| 4,776,027 A | * | 10/1988 | Hisano et al. | ............... 382/288 |
| 4,803,735 A | * | 2/1989 | Nishida et al. | .............. 382/151 |
| 4,817,166 A | * | 3/1989 | Gonzalez et al. | ............ 382/105 |
| 4,945,228 A | * | 7/1990 | Juvinall et al. | ........... 250/223 B |
| 5,412,203 A | * | 5/1995 | Toyama | ................... 250/223 B |
| 5,625,709 A | * | 4/1997 | Kasdan | ......................... 382/203 |
| 6,102,291 A | * | 8/2000 | Mazzone | ............... 235/462.01 |
| 6,867,799 B1 | * | 3/2005 | Broemmelsiek | ............. 348/169 |

FOREIGN PATENT DOCUMENTS

JP    A-9-108564    4/1997

* cited by examiner

*Primary Examiner*—Samir Ahmed
*Assistant Examiner*—Manav Seth
(74) *Attorney, Agent, or Firm*—Nixon & Vanderhye PC

(57) ABSTRACT

A position of a honeycomb structure, which is comprised of an outer shell, separation walls arranged in the form of a honeycomb within the outer shell, and a number of axially extending cells which are defined by the separation walls, is recognized. When the position recognition is carried out, the honeycomb structure is located with the axis extending in an upward and downward direction. A camera to pickup image data is disposed out of an area directly above an upper surface of the honeycomb structure in the axial direction. Image data including the entirety of the upper surface of the honeycomb structure is picked up by the camera, so that the position of the honeycomb structure is recognized based on the image data.

2 Claims, 8 Drawing Sheets

METHOD FOR RECOGNIZING POSITION OF HONEYCOMB STRUCTURE

BACKGROUND OF THE INVENTION

1. Field of the Invention

The present invention relates to a honeycomb structure position recognizing method in which a position of a honeycomb can be precisely recognized.

2. Description of the Related Art

In a motor vehicle, an exhaust gas purifying converter is provided in an exhaust system of an engine to purify the exhaust gas. As shown in FIG. 9, the exhaust gas purifying converter is comprised of a honeycomb structure 1 which is provided with an outer shell 11, separation walls 12 arranged in the form of a honeycomb within the outer shell 11, and a number of cells 13 which are defined by the separation walls 12 and which extend through the honeycomb structure 1.

In accordance with automaton of industrial equipment in recent years, for example, a position of the honeycomb structure 1 is recognized by a camera 92 in a conveyance line thereof using an automation, such as a robot. In the position recognition method of the honeycomb structure 1, the latter is located on a pallet 3, so that the axis direction D of the honeycomb structure is identical to the direction of gravity. Image data of the honeycomb structure 1 is picked up by the camera 92, so that the position of the honeycomb structure 1 can be recognized based on the image data and the honeycomb structure 1 is conveyed by the automaton.

However, the position recognition method of the honeycomb structure using the camera 92 has the following drawbacks.

Namely, the honeycomb structure 1 is provided with the plural separation walls 12 and cells 13 and, hence, when the honeycomb structure 1 is placed with the axial direction D identical to the vertical direction, little light can impinge upon the bottom portions 131 of the cells 13. When an image of the portion of the honeycomb structure 1 that is located directly below the camera 92 is taken by the camera 92, the photographed portion of the honeycomb structure 1 is the bottom portion 131.

Consequently, the portion of the honeycomb structure 1 that is placed directly below the camera 92 and that is photographed by the camera 92 is picked up as a dark image as indicated at 901 in FIG. 10 because this portion is directly viewed by the camera 92. The dark image portion 901 results in production of a noise signal having an adverse influence upon a precise position recognition of the honeycomb structure using the camera 92.

SUMMARY OF THE INVENTION

It is an object of the present invention to eliminate the drawbacks of the prior art by providing a position recognition method of a honeycomb structure in which the position of a honeycomb structure can be precisely recognized.

According to an aspect of the present invention, there is provided a position recognition method for recognizing a correct position of a honeycomb structure which is comprised of an outer shell, separation walls arranged in the form of a honeycomb within the outer shell, and a number of axially extending cells, which are defined by the separation walls, said honeycomb structure being located with the axis extending in an upward and downward direction, wherein a camera to pickup image data is disposed out of an area directly above an upper surface of the honeycomb structure in the axial direction, so that image data of at least a part of the upper surface of the honeycomb structure is picked up by the camera, whereby the position of the honeycomb structure is recognized based on the image data.

With this structure, the camera for picking up the image data is disposed out of the area directly above the upper surface of the honeycomb structure in the axial direction. Namely, in this invention, the camera is located in a position offset from the upward extensions of all the cells. Therefore, there is no possibility that the camera directly views the bottom portions of the cells of the honeycomb structure, so that the bottom portions are not included in the image data.

Therefore, when the image data including at least a part of the upper surface of the honeycomb structure is picked up by the camera, no dark image produced by directly viewing a bottom portion, as in the prior art, is contained in the image data. Consequently, it is possible to reduce the noise signal when the position of the honeycomb structure is recognized based on the image data.

Therefore, according to the present invention, the position of the honeycomb structure can be precisely recognized.

According to another aspect of the present invention, there is provided a position recognition method for recognizing a correct position of a honeycomb structure which is comprised of an outer shell, separation walls arranged in the form of a honeycomb within the outer shell, and a number of axially extending cells which are defined by the separation walls said honeycomb structure being located with the axis extending in an upward and downward direction, wherein the honeycomb structure is placed on a pallet of a color having a brightness different from that of the honeycomb structure, and a camera to pickup image data is disposed above the honeycomb structure, so that image data of at least a part of the upper surface of the honeycomb structure is picked up by the camera, whereby the position of the honeycomb structure is recognized based on the image data.

In this invention, the honeycomb structure is disposed on a pallet of a color having brightness different from the honeycomb structure. Namely, in this invention, the brightness of the color of the honeycomb structure is different from that of the pallet. Thus, it is possible to enhance the contrast between the honeycomb structure and the pallet. The boundary between the honeycomb structure and the pallet can be easily recognized due to the high contrast.

Consequently, for example, even if the dark image, produced when the camera located directly above the honeycomb structure directly views the bottom portion of the cell of the honeycomb structure, is included in the image data, an adverse influence upon the recognition of the correct position of the honeycomb structure, due to the noise signal caused by the dark image can be restricted.

Therefore, in the second aspect of the invention, the position of the honeycomb structure can be precisely recognized.

In the first or second aspect of the invention, the recognition method can be applied to recognition of the position of the honeycomb structure by a camera which is secured to stationary equipment or the like. The recognition method of the invention can be also applied to recognition of the position of the honeycomb structure relative to a movable machine such as a robot, by a camera which is secured to the robot, etc.

In the first aspect of the invention, the position recognition method can be applied to recognition of the position of the honeycomb structure relative to a pallet on which the honeycomb structure is disposed.

In the first aspect of the invention, it is preferable that the image data include the entirety of the upper surface of the honeycomb structure.

Consequently, the position of the honeycomb structure can be more precisely recognized, using the image data including the entirety of the upper surface of the honeycomb structure, i.e., the entire profile of the upper surface.

It is preferable that the camera be oriented toward the honeycomb structure, with the axis being inclined with respect to the axis of the honeycomb structure.

With this arrangement, in the first aspect of the invention, when the camera is located out of the area directly above the upper surface of the honeycomb structure in the axial direction, it is possible to direct the camera toward the honeycomb structure. Therefore, it is possible to obtain a relatively large image by stopping the field of view of the camera.

In the second aspect of the invention, the image data is preferably color data.

Consequently, it is possible to recognize the boundary between the honeycomb structure and the pallet, from the color data, relying not only upon the contrast therebetween but also upon the color difference. Thus, the position of the honeycomb structure can be correctly recognized.

The present invention may be more fully understood from the description of preferred embodiments of the invention set forth below, together with the accompanying drawing.

DESCRIPTION OF THE PREFERRED EMBODIMENTS

A first embodiment of the present invention will be first discussed below.

A honeycomb structure position recognition method according to a first embodiment of the present invention will be discussed below with reference to FIGS. 1 through 7.

Figure 1:
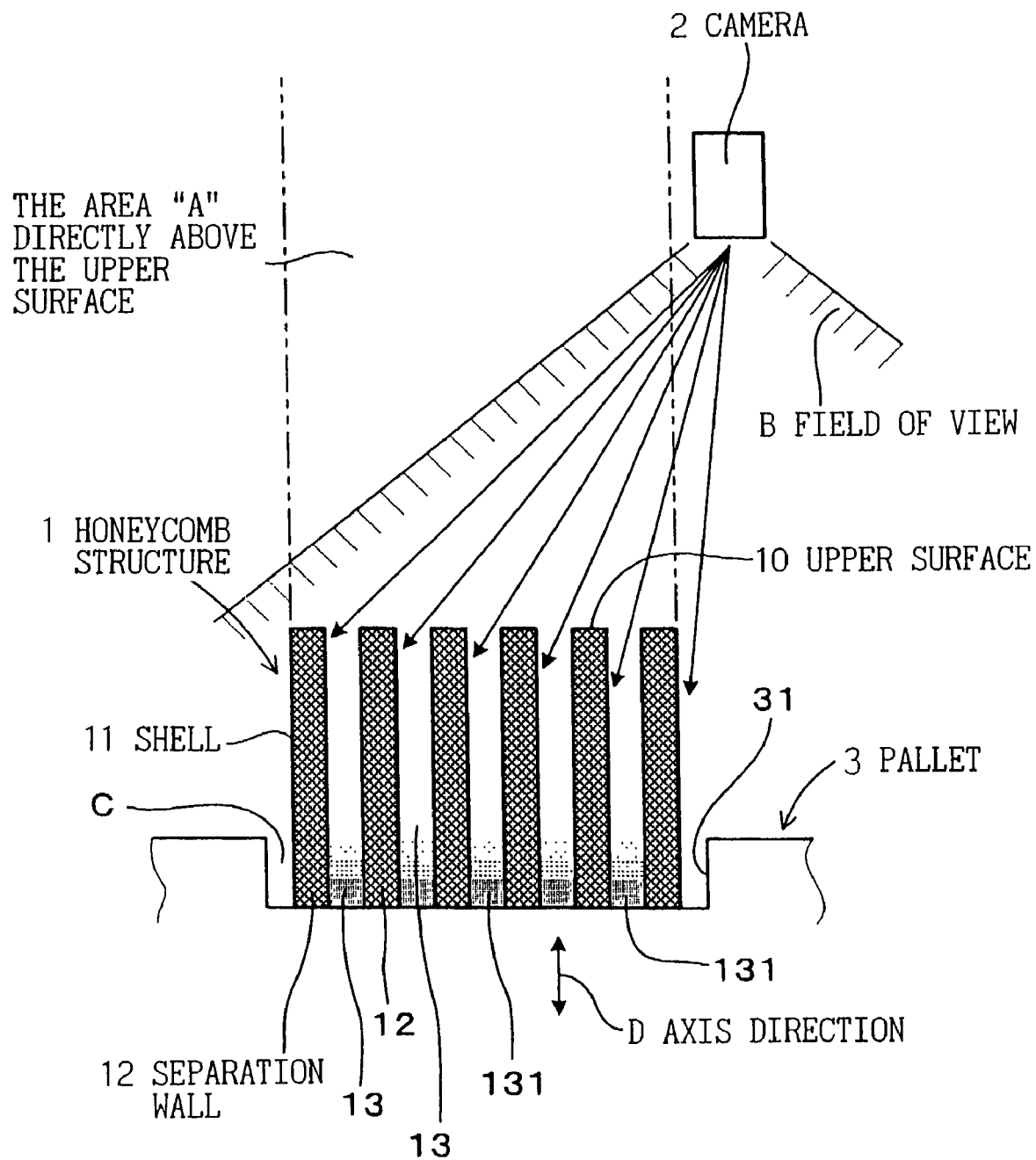
FIG. 1 is an explanatory view of a honeycomb structure position recognition method for a honeycomb structure according to a first embodiment of the present invention.

As can be seen in FIG. 1, a honeycomb structure position recognition method according to the first embodiment of the present invention is applied to a recognition of a position of a honeycomb structure 1 which is comprised of an outer shell 11, separation walls 12 which are arranged in a honeycomb within the outer shell 11, and a number of cells 13 which are defined by the separation walls 12 and which extend through the honeycomb structure 1 in the axis direction D. When the recognition of the position is carried out, the honeycomb structure 1 is placed so that the axis direction D is identical to the vertical direction.

In the first embodiment, the camera 2 to pick up the image data is disposed out of an area "A" located directly above the upper surface 10 of the honeycomb structure 1 in the axial direction D. The image data of the entirety of the upper surface 10 of the honeycomb structure 1 is picked up by the camera 2 to recognize the position of the honeycomb structure 1 based on the image data.

Note that in FIG. 1, the bottom portions 131 of the cells 13 of the honeycomb structure 1 are shadowed by the separation walls 12. This will be discussed below in detail.

Figure 10:
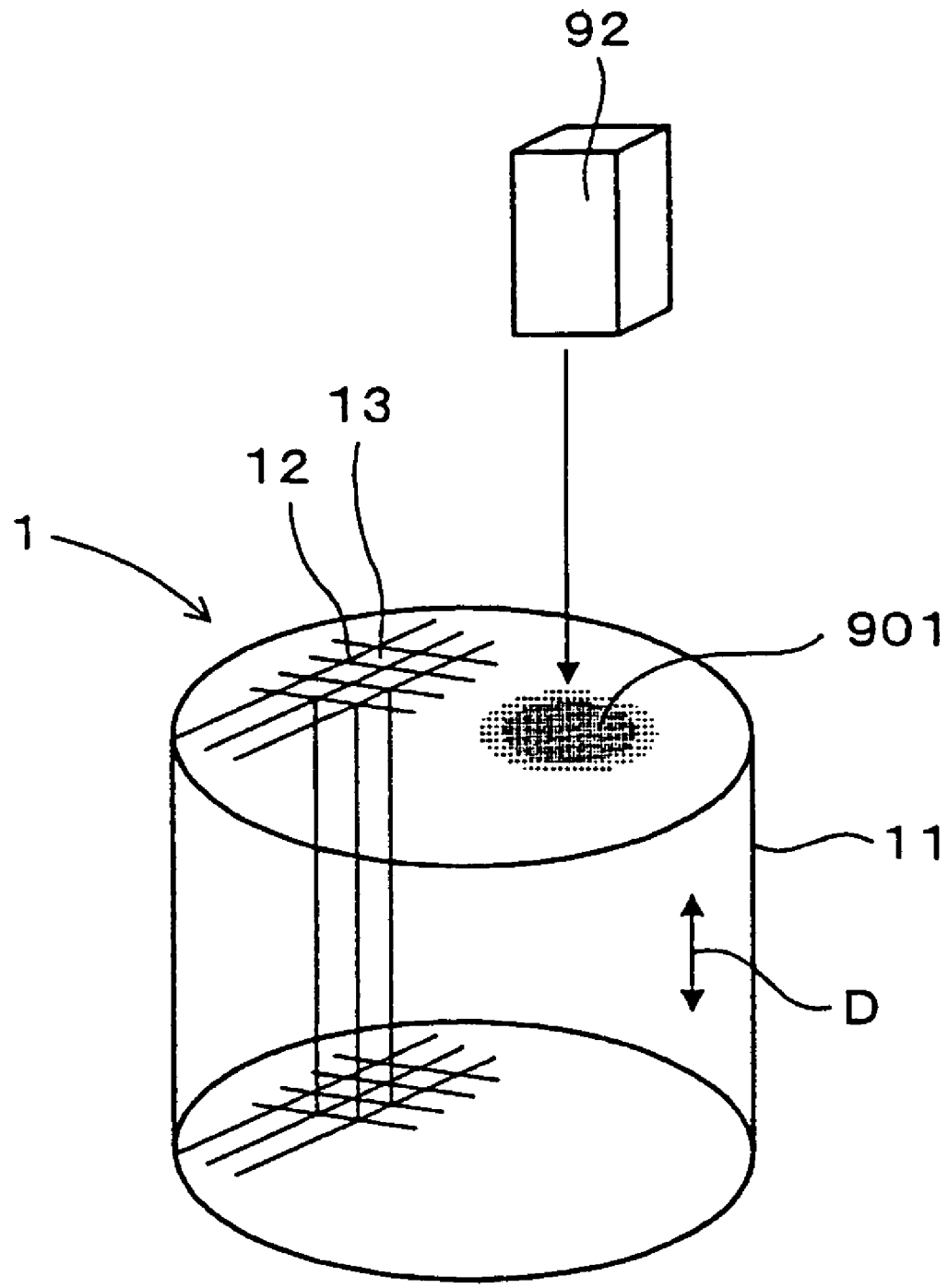
FIG. 10 is an explanatory view of a photographing operation, by a camera, wherein dark image portion produced by a shadow is picked up, in the prior art.

In the first embodiment of the present invention, the honeycomb structure 1 is in the form of a cylindrical pillar whose longitudinal axis is identical to the axis direction D and which is provided on its outer peripheral portion with the outer shell 11 (FIG. 10).

As shown in FIG. 1, a plurality of honeycomb structures 1 are placed in recessed placement portions 31 formed in a pallet 3. Each of the recessed placement portions 31 of the pallet 3 has a diameter larger than the diameter of the honeycomb structure 1, so that when the honeycomb structure 1 is placed in the recessed placement portion 31, there is a predetermined clearance C therebetween.

In this embodiment, the positions of the honeycomb structures 1 placed in the recessed placement portions 31 relative to the recessed placement portions 31 can be irregular due to the presence of the clearance C. Therefore, in this embodiment, the relative position of the honeycomb structure 1 to the recessed placement portion 31 is recognized by the camera 2.

Figure 2:
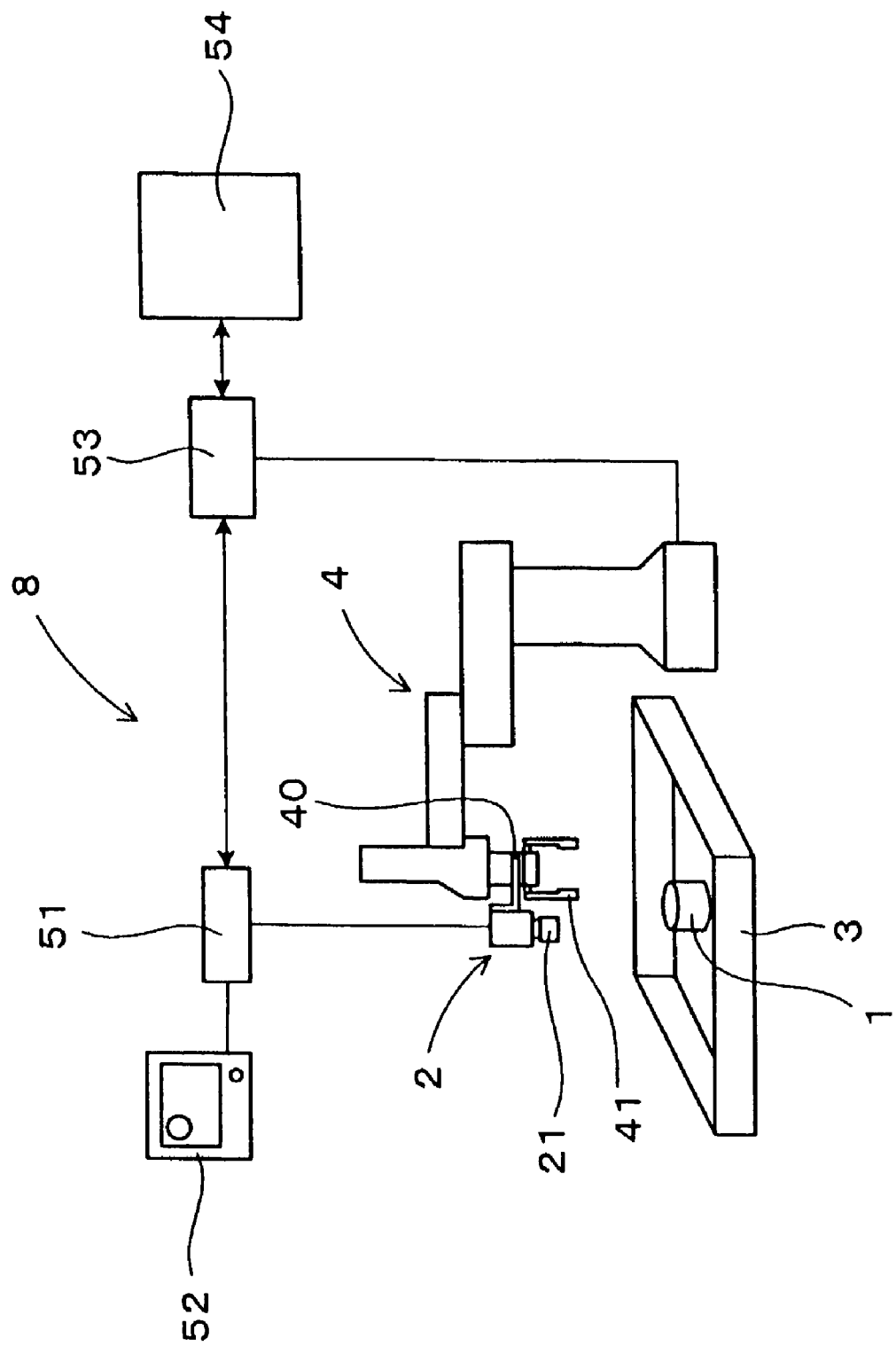
FIG. 2 is a schematic view of a position recognition apparatus, used in a honeycomb structure position recognition method, according to a first embodiment of the present invention.

As can be seen in FIG. 2, in a position recognition method of the present invention, a position recognition device 8 is used. In the position recognition device 8, the camera 2 is mounted to a robot 4, so that the position of the honeycomb structure 1 relative to the robot 4 is recognized.

The robot 4 has a chuck portion 41 with a front head 40 which can hold the honeycomb structure 1. The camera 2 in the illustrated embodiment is a CCD camera which is provided on its front end with a lens portion 21.

The robot 4 is set so that the head 40 thereof can move to the vicinity of the recessed placement portions 31 of the pallet 3 according to a teaching program, etc. The field of view B of the camera 2 is such that the when the head 40 of the robot 4 is disposed in the vicinity of the recessed placement portion 31, the lens portion 21 is out of the area "A" located directly above the upper surface 10 of the honeycomb structure 1 in the axis direction D (FIG. 1). The camera 2 picks up image data of the entirety of the upper surface 10 of the honeycomb structure 1 when the head 40 of the robot 4 is placed in the recessed placement portion 31.

As may be understood from the foregoing, according to the present invention, the positional deviation of the honeycomb structure 1 with respect to the pallet 3 can be corrected, using the position recognition method based on the image data.

The camera 2 is provided in the vicinity of the chuck portion 41 of the robot 4 and is connected to a visual device 51. The image data picked up by the camera 2 is sent to the visual device 51 to which a monitor 52 to display the image data picked up by the camera 2 is connected.

A robot controller 53 which controls the robot 4 is connected to a sequencer (equipment controller) 54 through parallel I/Os in the illustrated embodiment. The visual device 51 is connected to the robot controller 53 through RS232 in the illustrated embodiment.

The visual device 51 feeds back the image data picked up by the camera 2 to the robot controller 53 as position data. The robot controller 53 moves the head 40 of the robot 4 to a desired position relative to the honeycomb structure 1 placed on the pallet 3, so that the honeycomb structure 1 can be held by the chuck portion 41 provided on the head 40.

There is provided a lighting device (not shown) in the vicinity of the camera 2 to illuminate the honeycomb structure 1 to be photographed by the camera 2.

In the position recognition method of the illustrated embodiment, the image data of the honeycomb structure 1 is processed using a pattern matching method to thereby recognize the position of the honeycomb structure 1.

Figure 3:
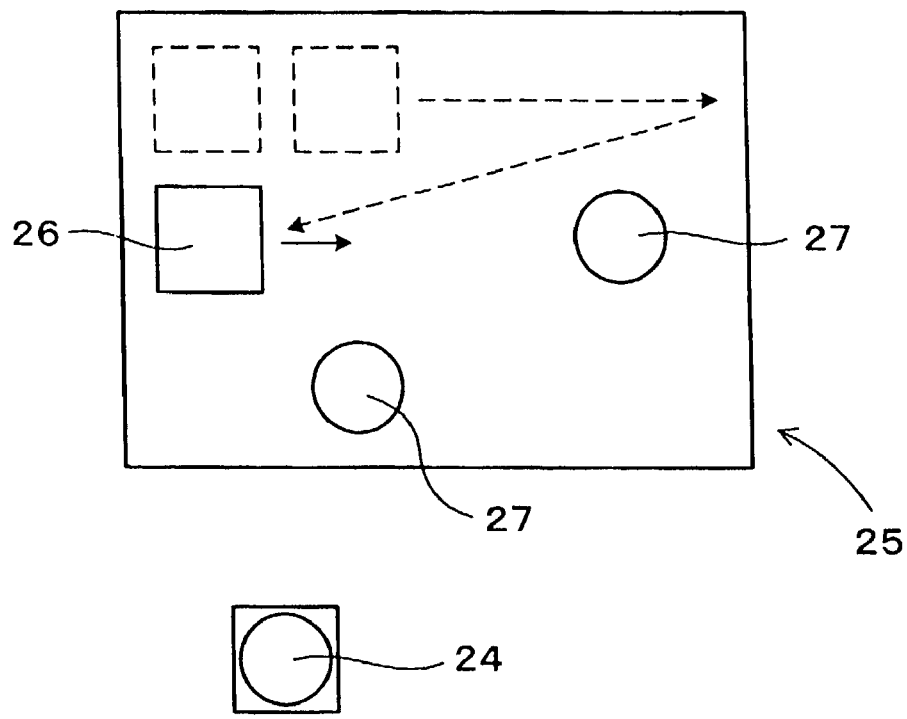
FIG. 3 is an explanatory view of a honeycomb structure position recognition method, using a pattern matching method, in a first embodiment of the present invention.

Namely, as shown in FIG. 3, in the pattern matching method, the shape of the upper surface of the honeycomb structure 1 in plan view is registered in advance as a master profile 24 in the visual device 51.

A search window 26 is moved in an image sent from the camera 2 to find a matching position 27 at which the image matches with the master profile 24 most. The visual device 51 recognizes the position of the honeycomb structure 1 relative to the chuck portion 41 of the robot 4, assuming that the honeycomb structure 1 is located in the matching position 27.

In the position recognition device 8, the head 40 of the robot 4 is moved to a position in which the chuck 41 can hold the honeycomb structure 1, so that the honeycomb structure 1 is held and moved by the chuck 41.

In the position recognition method of the first embodiment, the position of the honeycomb structure 1 can be recognized using image data processing methods other than the pattern matching method.

Namely, for example, the surface area of the image of the honeycomb structure 1 is obtained from the image data supplied from the camera 2, so that the position of the honeycomb structure 1 can be recognized based on the centroid in the surface area. Alternatively, it is also possible to determine edges of the profile of the honeycomb structure 1 based on the image data supplied from the camera 2 to thereby recognize the position of the honeycomb structure 1 based on the center of the edges.

Figure 4:
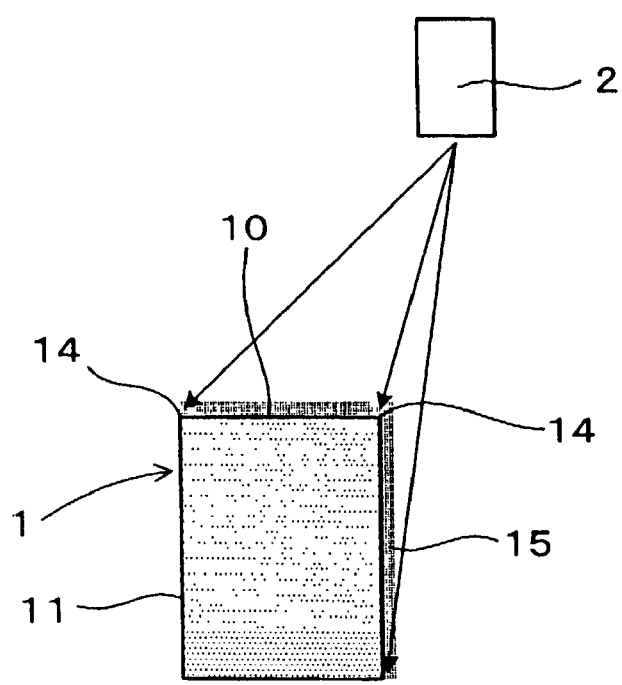
FIG. 4 is an explanatory view of a photographing operation by a camera, in a first embodiment of the present invention.
Figure 5:
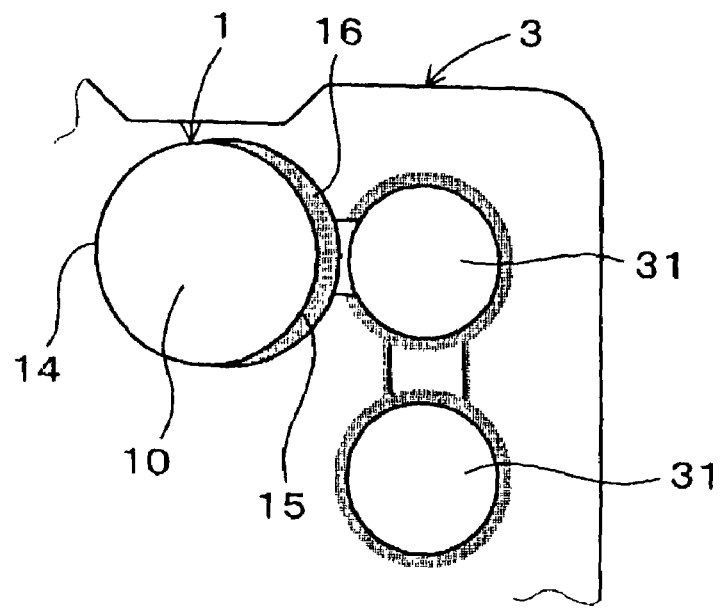
FIG. 5 is an explanatory view of image data, picked up by a camera, in a first embodiment of the present invention.

An alternative image processing method in which the image data 16 of the side surface 15 of the honeycomb structure 1 is used can be applied, as shown in FIGS. 4 and 5.

Namely, the camera 2 photographs the honeycomb structure 1 in an oblique direction in the illustrated embodiment and, hence it is possible to take pictures of both the upper surface 10 and the side surface 15, of the honeycomb structure 1. The image data 16 of the side surface 15 has a higher contrast with respect to the surrounding image than that of the profile data 14 of the upper surface 10. Therefore, the position of the honeycomb structure 1 can be more precisely recognized by the use of the image data 16 of the side surface 15.

Figure 6:
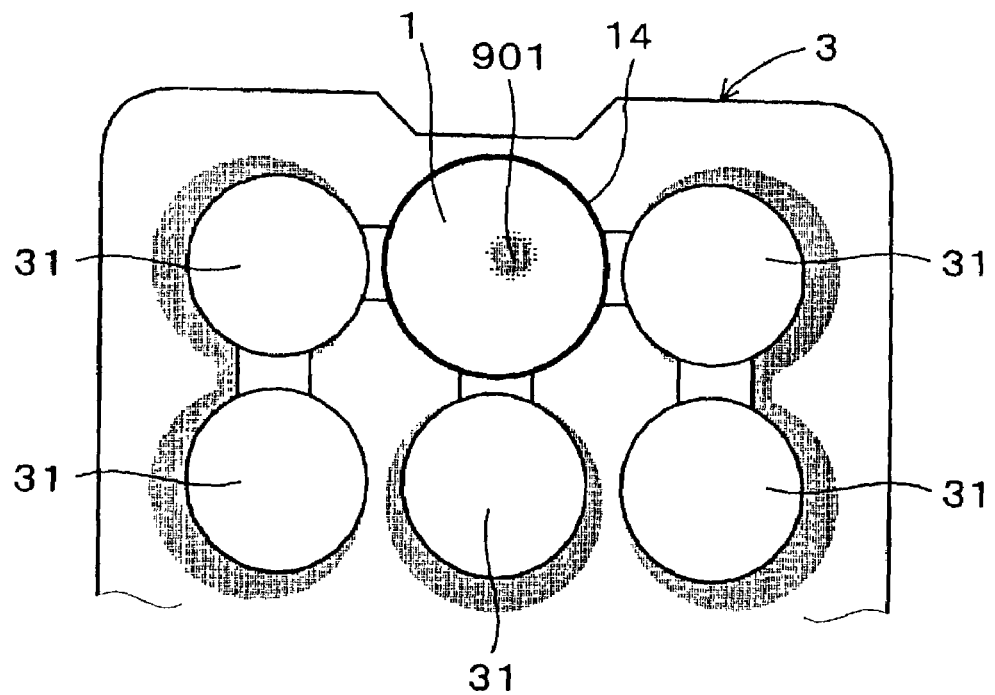
FIG. 6 is an explanatory view of image data picked up in a known honeycomb structure position recognition method.

For comparison, FIG. 6 shows image data of the honeycomb structure 1, picked up by the camera 2 when the lens portion 21 of the camera 2 is located in the area "A" directly above the upper surface 10 of the honeycomb structure 1 in the axis direction D, in the prior art. As can be seen from FIG. 6, the image includes a dark portion 901 produced by the bottom portion 131 of the honeycomb structure 1 which is directly viewed by the camera 2. Consequently, when an image processing operation, such as the pattern matching method is carried out, the dark image portion 901 has an adverse influence as a noise signal, upon a precise recognition of the position of the honeycomb structure 1.

Figure 7:
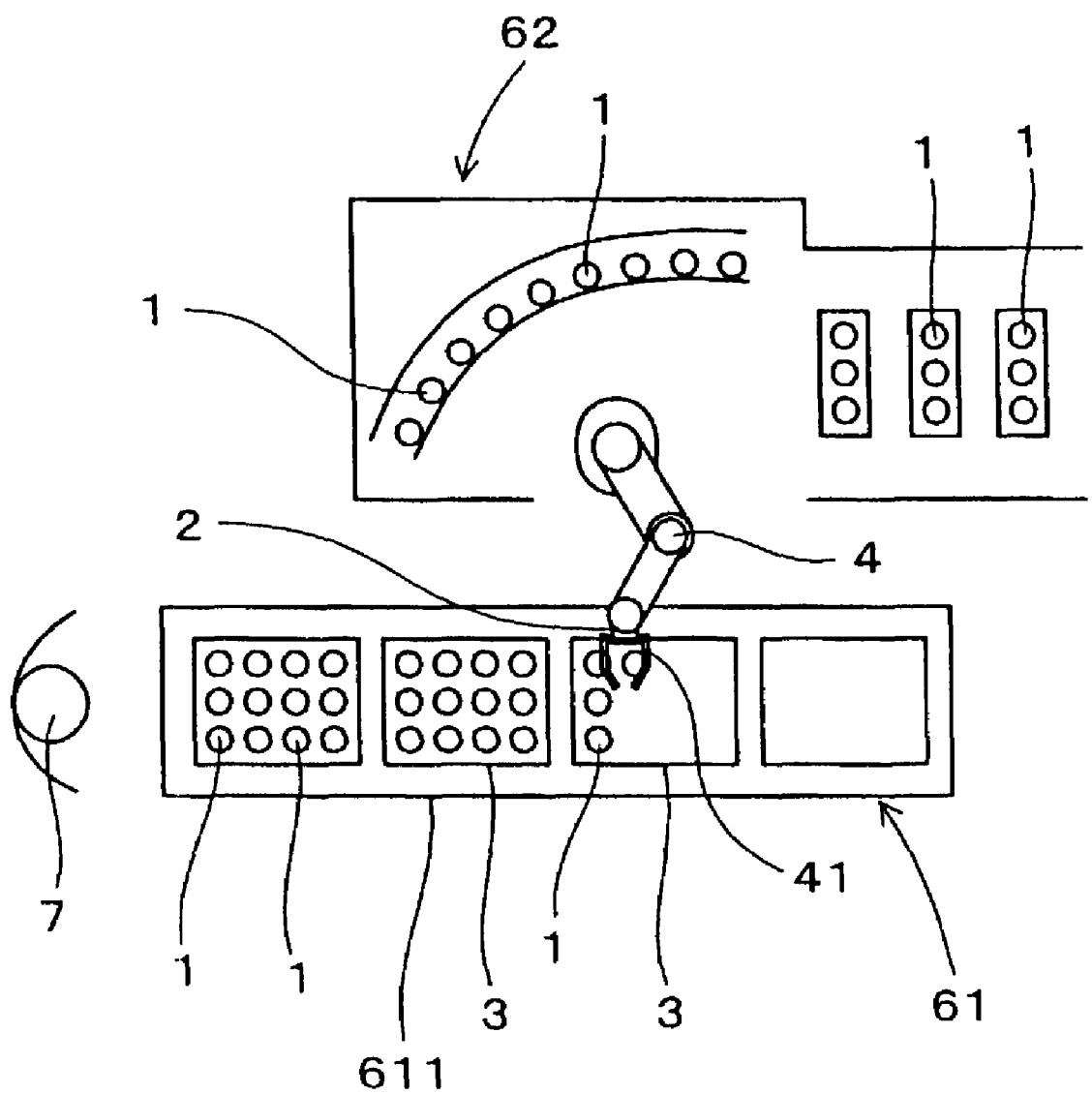
FIG. 7 is an explanatory view of a honeycomb structure position recognition method applied to a conveyance step which is carried out prior to an inspection step, in a first embodiment of the present invention.

As shown in FIG. 7, in the illustrated embodiment of the present invention, the position recognition method using the position recognition apparatus 8 is used in a conveyance station 61 prior to an inspection station 62 in which whether the shape, etc., of the honeycomb structure 1 produced after firing, or the like, is correct, is checked. In the conveyance station 61, the honeycomb structure 1 is held by the chuck portion 41 of the robot 4 and is conveyed to the inspection station 62.

In the conveyance station 61, an operator places the honeycomb structures 1 in the recessed placement portions 31 of the pallets 3, with the axis direction D being identical to the vertical direction, i.e., the direction of gravity. The placement can be easily carried out by the operator because there are desired clearances C between the honeycomb structures 1 and the recessed placement portions 31.

Thereafter, the pallets 3 having the honeycomb structures 1 placed thereon are conveyed by a conveyor 61 to the operating station of the robot 4. The head 40 of the robot 4 is moved to the vicinity of the recessed placement portion 31 of the pallet 3 in accordance with the position data set in the robot controller 53. In this position, the lens portion 21 of the camera 2 is located out of the area "A" directly above the upper surface 10 of the honeycomb structure 1, so that the image data of the entirety of the upper surface 10 of the honeycomb structure 1 can be picked up in an oblique upward direction.

The visual device 51 recognizes the position of the honeycomb structure 1 in the recessed placement portion 31, in accordance with the image data supplied from the camera 2, so that a positional deviation of the honeycomb structure 1 due to the clearance C can be recognized.

The positional deviation is fed back to the robot controller 53 which moves the head 41 of the robot 4 to a correct position in which the chuck 41 of the robot 4 can hold the honeycomb structure 1.

The robot 4 holds the honeycomb structure 1 by the chuck 41 of the head 40 and conveys the honeycomb structure 1 to the inspection station 62. In the inspection station 62, the shape, etc., of the honeycomb structure 1 is inspected.

In the illustrated embodiment, the camera 2 is not located in the area "A" directly above the honeycomb structure 1 and, hence, there is no possibility that the camera 2 directly views the bottom portions 131 of the cells 13 of the honeycomb structure 1. Consequently, in the present invention, the bottom portions 131 are not included in the image data.

Therefore, when the image data of the upper surface 10 of the honeycomb structure 1 is picked up by the camera 2, no dark image 901 caused by the direct viewing of the bottom portions 131 can be included in the image data, unlike the prior art. Thus, it is possible to minimize the noise signal when the position of the honeycomb structure 1 is recognized based on the image data Consequently, according to the position recognition method of the present invention, the position of the honeycomb structure 1 can be precisely recognized.

In the illustrated embodiment, it is possible to correct the positional deviation of the honeycomb structure 1 relative to the recessed placement portion 31 of the pallet 3, due to the clearance C therebetween. Therefore, it is possible to move the chuck portion 41 of the robot 4 to a correct position relative to the honeycomb structure 1. Consequently, the chuck portion 41 of the robot 4 can smoothly hold the honeycomb structure 1. Thus, no sudden collision of the chuck portion 41 with the honeycomb structure 1 occurs and, hence, it is possible to prevent the honeycomb structure 1 from being damaged or cracked by collision with the chuck portion 41.

A second embodiment of the invention will be discussed below.

Figure 8:
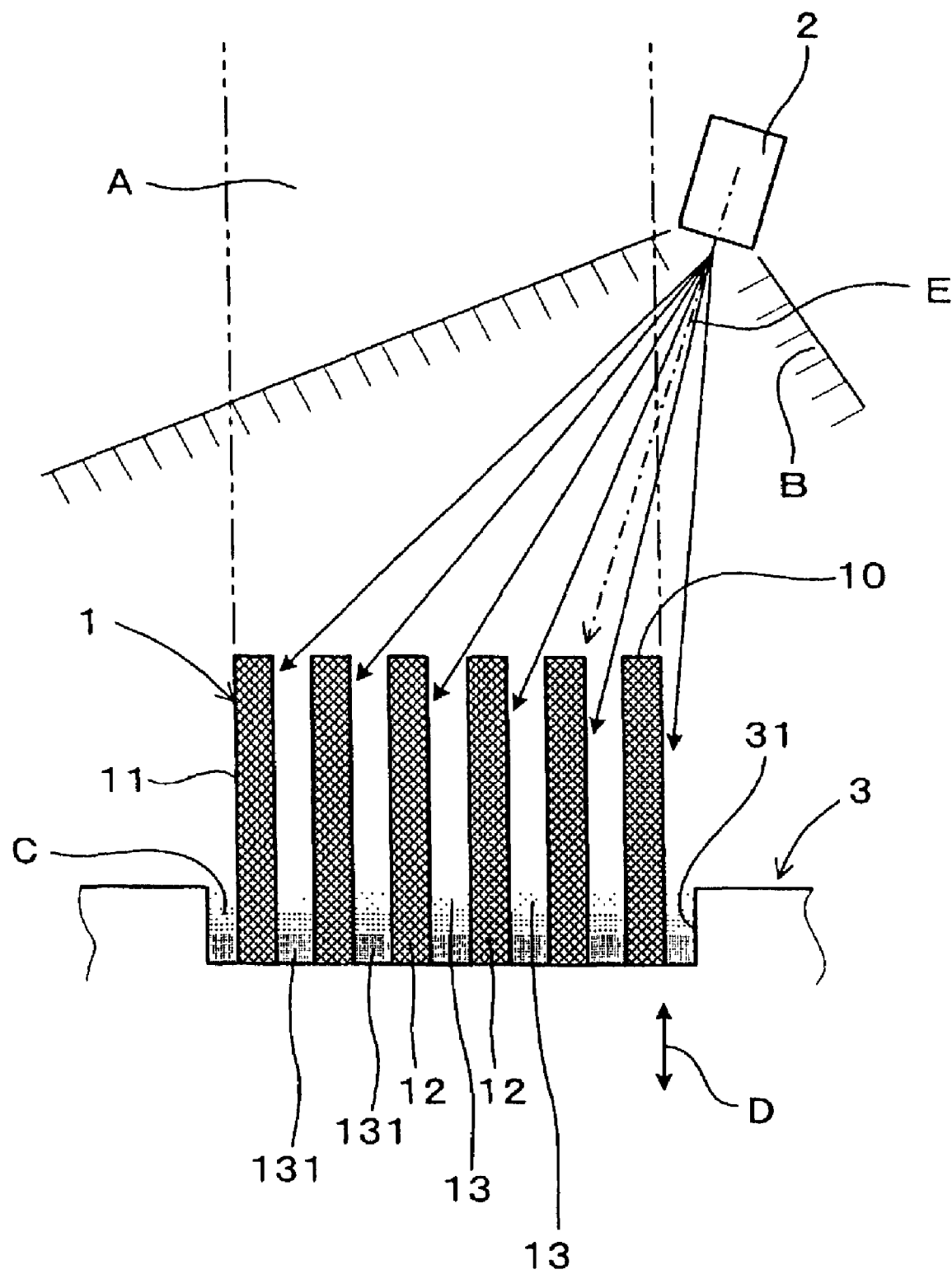
FIG. 8 is an explanatory view of a honeycomb structure position recognition method according to a second embodiment of the present invention.
Figure 9:
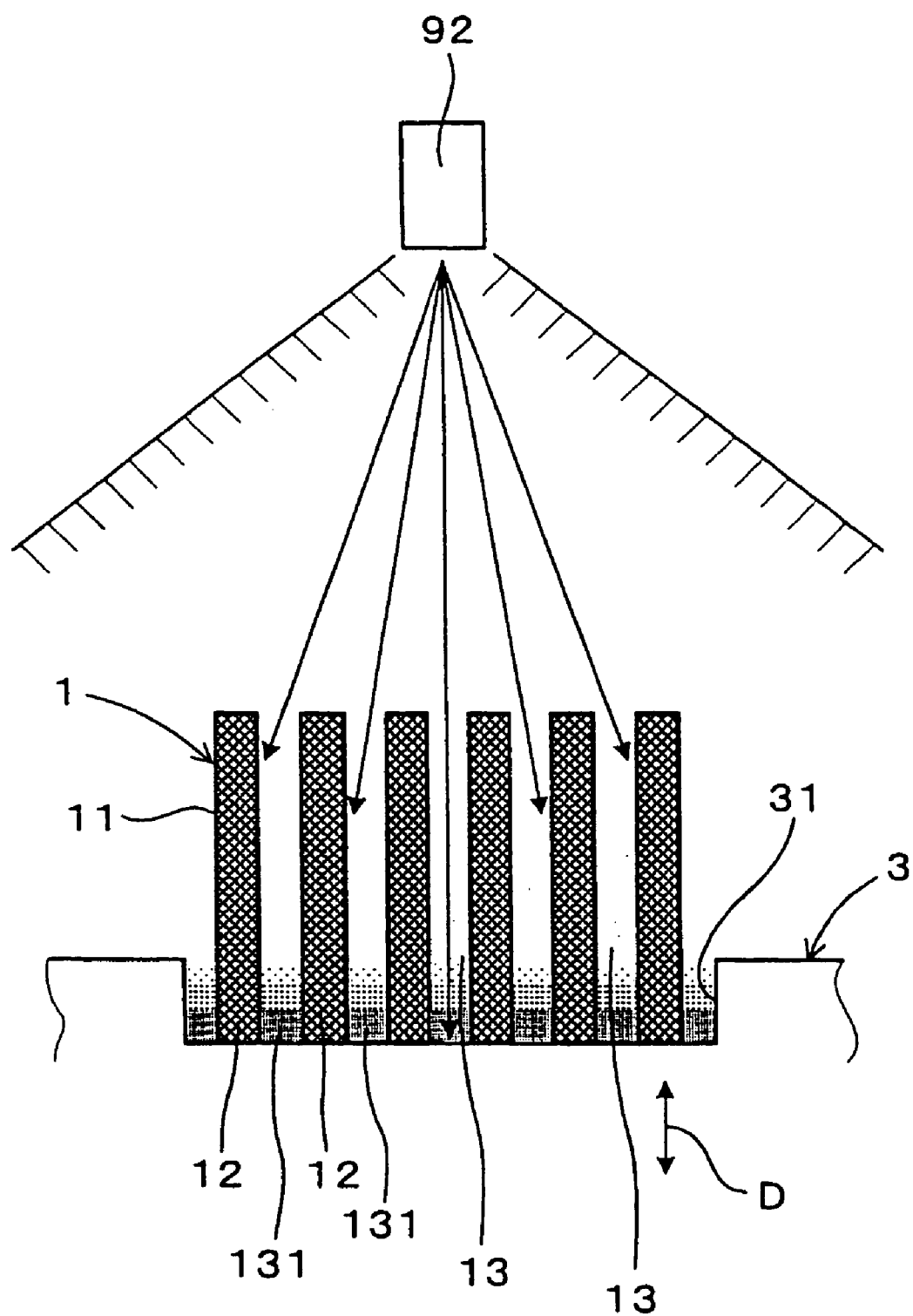
FIG. 9 is an explanatory view of a honeycomb structure position recognition method according to the prior art.

As shown in FIG. 8, in the second embodiment, the robot 4 is moved to move the camera 2 to a position in which the camera 2 is out of the area "A" directly above the upper surface 10 of the honeycomb structure 1 and is inclined with respect to the axis direction D of the honeycomb structure 1 so that the center axis E of the field of view is oriented toward the honeycomb structure 1 to pick up the image data of the latter. Other structures of the second embodiment are the same as those of the first embodiment.

In the second embodiment, when the camera 2 is disposed out of the area "A" directly above the upper surface 10 of the honeycomb structure 1, the camera 2 can be oriented toward the honeycomb structure 1. Therefore, it is possible to obtain a relatively large size of an image of the honeycomb structure by stopping the field of view of the camera 2.

The same mode of operation and technical effects as those of the first embodiment can be obtained in the second embodiment.

A third embodiment of the invention will be discussed below.

In the position recognition method according to the third embodiment, a pallet 3 having a color of different brightness than the honeycomb structure 1 is used to recognize the position of the honeycomb structure 1. Moreover, in the third embodiment, the color of the pallet 3 has a lower brightness than that of the honeycomb structure 1. The image data is picked up when the camera 2 is moved to a position above the honeycomb structure 1 by moving the robot 4.

In the third embodiment, the image data picked up by the camera 2 is color information. Other structures of the third embodiment are the same as those of the first embodiment.

In the third embodiment, the honeycomb structure 1 and the pallet 3 are different in the color brightness. Therefore, it is possible to enhance the contrast of the honeycomb structure 1 and the pallet 3. The enhancement of the contrast makes it possible to easily recognize the boundary between the honeycomb structure 1 and the pallet 3.

Therefore, for instance, even if the camera 2 is located in the area "A" directly above the honeycomb structure 1, so that the dark image 901 produced by direct viewing of the bottom portion 131 of the cell 13 of the honeycomb structure 1 is included in the image data, the noise signal produced by the dark image 901 has little influence on the precise recognition of the position of the honeycomb structure 1.

Therefore, the position of the honeycomb structure 1 can be precisely recognized by the position recognition method of the third embodiment of the invention.

While the invention has been described by reference to specific embodiments chosen for purposes of illustration, it should be apparent that numerous modifications could be made thereto by those skilled in the art without departing from the basic concept and scope of the invention.

What is claimed is:

1. A position recognition method for recognizing a correct position of a honeycomb structure which is comprised of an outer shell, separation walls arranged in the form of a honeycomb within the outer shell, and a number of axially extending cells which are defined by the separation walls, said honeycomb structure being located with the axis extending in an upward and downward direction, wherein the honeycomb structure is placed on a pallet of a color having a brightness different from that of the honeycomb structure, and a camera to pickup image data is disposed above the honeycomb structure, so that image data of at least a part of the upper surface of the honeycomb structure is picked up by the camera, the camera being disposed at a position where the camera directly views the pallet, on which the honeycomb structure is arranged, through the cells of the honeycomb structure, whereby the position of the honeycomb structure is recognized based on the image data, wherein the pallet is of a color having lesser brightness than the honeycomb structure.

2. A position recognition method according to claim 1, wherein the image data is color data.

* * * * *